United States Patent [19]
Hong et al.

[11] Patent Number: 5,900,367
[45] Date of Patent: May 4, 1999

[54] METHOD FOR PURIFYING TAXOL FROM TAXUS BIOMASS

[75] Inventors: Seung-Suh Hong; Bong-Kyu Song; Jin-Hyun Kim; Chang-Bae Lim, all of Taejon; Hyun-Soo Lee, Seoul; Kwang-Wook Kim, Taejon; In-Seon Kang, Seoul; Hung-Bok Park, Kyonggi-Do, all of Rep. of Korea

[73] Assignee: Samyang Genex Co., Ltd., Seoul, Rep. of Korea

[21] Appl. No.: 08/652,493

[22] PCT Filed: Apr. 27, 1996

[86] PCT No.: PCT/KR96/00059

§ 371 Date: May 28, 1996

§ 102(e) Date: May 28, 1996

[87] PCT Pub. No.: WO96/34973

PCT Pub. Date: Nov. 7, 1996

[30] Foreign Application Priority Data

Apr. 29, 1995 [KR] Rep. of Korea ............... 95-10455
Feb. 3, 1996 [KR] Rep. of Korea ............... 96-2621
Feb. 3, 1996 [KR] Rep. of Korea ............... 96-2622

[51] Int. Cl.$^6$ ................ C12P 17/02; A61K 35/78
[52] U.S. Cl. ............... 435/123; 549/510; 549/511; 424/195.1
[58] Field of Search ................ 435/123, 240.4, 435/240.46, 240.48; 424/195.1; 549/510, 511

[56] References Cited

U.S. PATENT DOCUMENTS

| | | | |
|---|---|---|---|
| 5,279,949 | 1/1994 | Nair . | |
| 5,475,120 | 12/1995 | Rao . | |
| 5,478,736 | 12/1995 | Nair | 435/123 |
| 5,480,639 | 1/1996 | ElSohly | 424/195.1 |

FOREIGN PATENT DOCUMENTS 0553 780 A1  8/1993  European Pat. Off. .

OTHER PUBLICATIONS

D. R. Wu et al., Preparative Separation of Taxol in Normal and Reversed–Phase Operations, Journal of Chromatoraphy A, 702:233–241(1995).

S.D. Harvey et al, Separation of Taxol from Related Taxanes in *Taxus brevifolia* Extracts by Isocratic Elution Reversed–Phase Microcolumn High–Performance Liquid Chromatograph, Journal of Chromatography, 587:300–305(1991).

K.V. Roa, Taxol and Related Taxanes. I.Taxanes of *Taxus brevifolia* Bark, Pharamceutical Research, 10(4):521–524 (1993).

J.H. Cardellina II, HPLC Separation of Taxol and Cephalomannine, Journal of Chromatograph, 14(4):659–665 (1991).

K.V. Rao et al., A new Large–Scale Process for Taxol and Related Taxanes from *Taxus brevifolia*, Pharmaceutical Research, 12(7):1003–1010(1994).

G.P. Guanawaruana et al., Isolation of 9–dihydro–13–acetylbaccatin III from *Taxus canadensis*, Journal of Natural Product, 55(11):1686–1689(1992).

The Merck Index, Tenth Edition, 1983, p. 4164.

*Primary Examiner*—Irene Marx
*Attorney, Agent, or Firm*—Darby & Darby

[57] ABSTRACT

The present invention relates to a rapid and simple method for mass production of taxol from the cell culture of Taxus genus plant with a high purity and recovery. The method for mass production of taxol from Taxus genus plant of the present invention, comprises the steps of: (i) organic solvent extraction of biomass from Taxus genus plant to obtain a crude extract; (ii) synthetic adsorbent treatment of the crude extract and filtration to give filtrate; (iii) addition of hexane to the filtrate to precipitate crude taxol; (iv) fractional precipitation of the crude taxol in a mixture of alcohol and water and vacuum drying the precipitate to obtain taxol powder; and, (v) high performance liquid chromatography of the taxol powder. According to the method of the present invention, taxol of over 99% purity can be simply obtained from Taxus genus plant with a high recovery of over 90%.

15 Claims, No Drawings

METHOD FOR PURIFYING TAXOL FROM TAXUS BIOMASS

This application was filed under 35 USC 371 as the national phase of PCT KR96/00059, filed Apr. 27, 1996.

BACKGROUND OF THE INVENTION

1. Field of the Invention

The present invention relates to a method for mass production of taxol from Taxus genus plant, more specifically, to a rapid and simple method for mass production of taxol with a high purity and recovery, which comprises the steps of solvent extraction of biomass from Taxus genus plant employing methanol, dichloromethane and hexane, adsorbent treatment, precipitation in hexane, fractional precipitation and high performance liquid chromatography.

2. Description of the Prior Art

Taxanes are diterpene compounds containing the taxane skeleton. For example, taxol is famous as the first identified compound with a taxane ring which is effective for the treatment of leukemia and cancer. Recently, it has been reported that taxol Xs capable of curing approximately 30%, 50% and 20% of ovarian, breast and lung cancer patients, respectively. Also, taxane compounds include baccatin III, 10-deacetylbaccatin III, 10-deacetyltaxol, cephalomannine and deacetylcephalomannine, which are employed in the semi-synthesis of taxol.

Taxane compounds are represented as general formula (I) and (II) as followings:

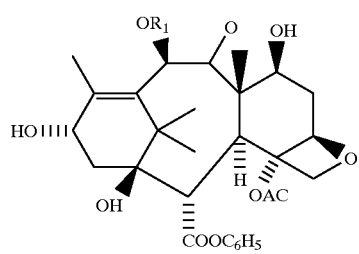

(I)

wherein, if $R_1$=AC, the compound is baccatin III; and, if $R_1$=OH, the compound is 10-deacetylbaccatin III.

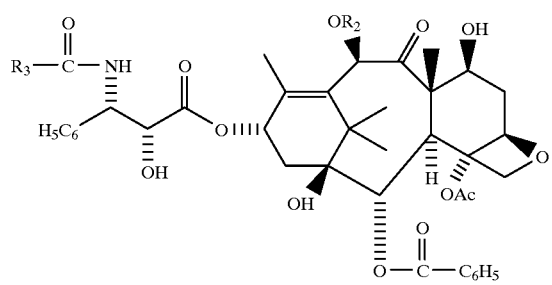

(II)

wherein, if $R_2$=AC, $R_3$=$C_6H_5$, the compound is taxol;
if $R_2$=OH, $R_3$=$C_6H_5$, the compound is 10-deacetyltaxol;
if $R_2$=AC, $R_3$=$CH_3CH$=$CH(CH_3)$, the compound is cephalomannine; and,
if $R_2$=OH, $R_3$=$CH_3CH$=$CH(CH_3)$, the compound is 10-deacetylcephalomannine.

On the other hand, total synthesis, semi-synthesis and extraction methods have been employed to prepare taxol.

The total synthesis method, however, has not been practically applied in the art, since it requires very expensive chemical reagents and the yield is not so high, which can be expected from the complicated chemical structure of taxol.

The semi-synthesis method employing precursors such as 10-deacetylbaccatin III, has revealed some drawbacks since it essentially entails complicated and multiple steps of isolating and purifying taxol precursors from Taxus genus plant and transforming the taxol precursors to taxol, which, in turn, has been an obstacle to the universal use of the method.

Accordingly, extraction methods by which taxol can be isolated from Taxus genus plants in a direct manner, have prevailed in the art, since they have the advantage of economy, and a variety of approaches have been described in the art:

WO 94/12268 discloses a method of isolating taxol by employing a semi-permeable membrane and reverse osmosis apparatus. However, said method has revealed a serious problem that it essentially requires the expensive semi-permeable membrane and reverse osmosis apparatus accompanied by complicated techniques for operating them.

EP 553,780 A teaches a method of isolating taxol and precursor thereofs which comprises the steps of vacuum drying a methanol extract of Taxus genus plant, solvent extraction employing cyclohexane and methylenechloride to give crude taxol followed by silica gel column HPLC.

WO 92/18492 describes a method of purifying taxol which comprises the steps of methanol extraction of Taxus genus plant, partitional fractionation employing methylenechloride or ethylacetate to obtain crude taxol and normal-phase liquid chromatography.

WO 92/07842 illustrates a method isolating taxol which comprises the steps of a series of solvent extractions employing ethanol, chloroform and methanol to give crude taxol followed by reverse-phase HPLC.

WO 94/13827 suggests a method of purifying taxol which comprises the steps of organic solvent extraction using ethanol, methanol and acetone, adsorbent treatment of activated carbon or charcoal to give crude taxol followed by normal-phase liquid chromatography.

JP 6-157329 A offers a method of obtaining crude taxol of low-purity which comprises a series of solvent extractions employing ethylacetate, ether, acetonitrile and acetone.

However, all of the prior art purification methods, which primarily aim to obtain crude taxol of low-purity by employing solvent extraction and chromatography works, essentially provide taxol-related compounds such as terpenoids, lipids, chlorophyll and phenols, accompanying the taxol of interest. Accordingly, high-purity of taxol has not been obtained even in the case of employing so many chromatographic columns, leading to a heavy load of impurities on the columns used in the purification steps.

Moreover, since the purity of taxol thus obtained is not high, solubility in organic solvent is naturally so low that recovery and yield in the course of chromatography can not be controlled and extra steps for crystallization are essentially required to obtain high-purity crystallized taxol. Accordingly, the prior art purification methods have not been practically employed in the art and there has been a continuous need in the art to develop a method for isolating high-purity taxol in a more simple and economical manner.

SUMMARY OF THE INVENTION

In accordance with the present invention, the inventors developed a method of purifying taxol from Taxus genus plant by employing a series of solvent extractions, adsorbent treatment, fractional precipitation and high performance liquid chromatography.

A primary object of the present invention is, therefore, to provide a rapid and simple method for mass production of taxol from Taxus genus plant with a high purity of over 99% and a high recovery of over 90% by employing small amounts of organic solvent, regardless of the water content in biomass.

DETAILED DESCRIPTION OF THE INVENTION

The method for mass production of taxol from Taxus genus plant of the present invention, comprises the steps of:
(i) organic solvent extraction of biomass from Taxus genus plant to obtain a crude extract;
(ii) synthetic adsorbent treatment of the crude extract and filtration to give filtrate;
(iii) addition of hexane to the filtrate to precipitate crude taxol;
(iv) fractional precipitation of the crude taxol in a mixture of alcohol and water and drying the precipitate to obtain taxol powder; and,
(v) high performance liquid chromatography of the taxol powder.

Biomass employed in the present invention as starting material includes: the leaf or bark of Taxus genus plant which is chopped and powdered and the cake of cell mass obtained in tissue culture of Taxus genus plant, where Taxus genus plant covers *Taxus brevifolia, Taxus canadensis, Taxus cuspidata, Taxus baccata, Taxus globosa, Taxus floridana, Taxus wallichiana, Taxus media* and *Taxus chinensis*, regardless of the water content in the biomass.

The method for mass production of taxol of the invention is described in more detail, in accordance with the purification steps.

Step 1: Organic Solvent Extraction

As a preferred embodiment of the present invention, the solvent extration is carried out employing methanol and dichloromethane as follows:

The biomass of Taxus genus plant is added to methanol, stirred at room temperature for 20 to 60 min, preferably 30 to 40 min and filtered to give a methanol extract, where the biomass is preferably added to methanol at a ratio of 20 to 200% (w/v), preferably 40 to 140% (w/v), most preferably 100% (w/v), and extraction is repeated at least 3 times, preferably 4 times. Then, the methanol extracts obtained from each time, are collected and concentrated at a temperature of 20 to 40° C. under a reduced pressure of 1 to 30 mmHg, to reduce the volume of the methanol extract to 20 to 30% of original. At this time, careful attention should be drawn to control the temperature in a range of 20 to 40° C., since epimerization of taxol and taxol derivatives may be accelerated at a temperature of over 40° C. To the concentrated methanol extract is added dichloromethane at a volume ratio of 10 to 50%, preferably 20 to 30%, stirred at room temperature for 10 to 20 min, and left to stand to obtain a crude extract. Extraction is repeated at least 2 times, preferably 3 times and the crude extracts thus obtained are pooled and dried at 20 to 40° C. under a reduced pressure of 1 to 30 mmHg.

Alternatively, the solvent extraction can be carried out by employing dichloromethane/methanol, methanol and hexane as followings:

The biomass of Taxus genus plant is added to a mixture of dichloromethane/methanol, stirred at room temperature for 20 to 60 min, preferably 30 to 40 min and filtered to give a dichloromethane/methanol extract. At this moment, dichloromethane and methanol are preferably mixed at a volume ratio of 7:3 to 9:1, preferably 8:2 to 9:1, most preferably 9:1, and the biomass is added to the mixture at a ratio of 10 to 100% (w/v), preferably 15 to 50% (w/v). Then, the extraction and concentration are carried out analogously as in the Solvent extraction illustrated above. The concentrated extract is dissolved in methanol at a ratio of 50 to 200% (w/v), preferably 70 to 150% (w/v), more preferably 90 to 110% (w/v), to obtain methanol extract. The methanol extract is added to hexane at a volume ratio of 5 to 30%, preferably 7 to 20%, more preferably 8 to 15%, stirred at room temperature for 10 to 20 min and left to stand, and followed by the removal of hexane layer to obtain a crude extract.

Step 2: Adsorbent Treatment

Since the impurities such as tar in the dried crude extract obtained in step 1, play an obstructive role in a subsequent purification step, synthetic adsorbent is added to remove the impurities. To the crude extract is dissolved in dichloromethane at a ratio of 5 to 100% (w/v), preferably 10 to 50% (w/v), more preferably 15 to 25% (w/v) and followed by the addition of the synthetic adsorbent at a ratio of 10 to 200% (w/w), preferably 30 to 100% (w/w), most preferably 50% (w/w), stirred at 30 to 40° C. for 10 to 40 min and filtered with the said synthetic adsorbent to obtain filtrate. The synthetic adsorbents used are active clay, activated charcoal and activated carbon, etc., from which active clay is most preferably used. The filtrate thus obtained is washed with a proper amount of dichloromethane several times and washings are combined with the filtrate. Then, the filtrate thus combined is concentrated at 30 to 40° C. under a reduced pressure of 1 to 30 mmHg to the level equivalent to 150 to 200% of the crude extract prior to adsorbent treatment.

Step 3: Precipitation in Hexane

The filtrate obtained in step 2 is added to 500 to 1,500% volume of hexane, preferably 700 to 1,200%, most preferably 1,000% to obtain the precipitate, and filtrated to give crude taxol whose taxol content is over 23%.

Step 4: Fractional Precipitation

The crude taxol obtained in the previous step, is dissolved in a mixture of alcohol and distilled water at a ratio of 1 to 10% (w/v) and left to stand at −20 to 10° C. for 1 to 3 days to obtain taxol precipitate. Then, the resultant precipitate is filtered and dried at 20 to 40° C. for 1 to 3 hrs under a vacuum condition, to give taxol powder. At this moment, methanol and distilled water are preferably mixed at a volume ratio of 2:1 to 1:1. The fractional precipitation is repeated several times, preferably at least 2 times to obtain taxol of over 85% purity, which also guarantees high recovery and purity while minimizing the load borne on the columns employed in a subsequent HPLC step.

Step 5: High Performance Liquid Chromatography (HPLC)

HPLC step is composed of an HPLC employing a hydrophobic resin column, e.g., ODS (octadecylsilylated, $C_{18}$) column to remove non-polar impurities, and an HPLC employing a silica column to remove polar impurities.

In an HPLC employing a hydrophobic resin column, taxol powder dissolved in organic solvent is loaded on the hydrophobic resin column, e.g., ODS, and elution is made with a mixture of methanol and water. Then, the eluates are analyzed by UV detector by determining absorbances at 227 nm and active fractions containing taxol are pooled, and dried under a vacuum condition for a subsequent use in silica HPLC. At this time, taxol powder is dissolved in dimethylsulfoxide (DMSO) or methanol at a ratio of 0.5 to 10% (w/v), preferably 1 to 2% (w/v) and methanol and water are mixed at a volume ratio of 1:0.3 to 1:0.8, preferably 1:0.4 to 1:0.7, more preferably 1:0.5 to 1:0.6. Samples are injected onto the HPLC at a speed of 3 to 5 cm/min at a concentration of 50 to 150 mg/ml (in methanol).

In an HPLC employing a silica column, taxol containing fractions obtained in the previous HPLC work, are injected onto the silica column and eluted with a mixture of dichloromethane and methanol. Then, the eluates are analyzed by a UV detector by determining absorbances at 227 nm and active fractions are pooled, and dried under a vacuum condition to give the crystallized taxol. At this time, samples are injected onto the HPLC at a concentration of 50 to 150 mg/ml (in $CH_2Cl_2$), and eluted with a mixture of dichloromethane and methanol mixed at a volume ratio of 95:5 to 99:1, preferably 98:2 to 99:1, most preferably 99:1. The HPLC steps finally produce taxol crystals of over 99% purity with a recovery of over 90%.

Quantitative Analysis of Taxol

Taxol which is purified from Taxus genus plant according to the method of the present invention, is quantitatively assayed by employing high performance liquid chromatography under a specific condition described in Table 1 below.

TABLE 1

| Condition for quantitative assay of taxol | |
| --- | --- |
| Instrument | HPLC (Waters, U.S.A.) |
| Column | Capcell Pack $C_{18}$ UG 120 (length: 250 mm, inner diameter: 4.6 mm) |
| Column temp. | 40° C. |
| Mobile phase | $CH_3CN$: water (20~100% gradient) |
| Fluid speed | 1.0 ml/min |
| Injection volume | 10 μl |
| Detector | UV (227 nm), ATTE = 3 |

The present invention is further illustrated in the following examples, which should not be taken to limit the scope of the invention.

EXAMPLE 1
Purification of Taxol from the Tissue Culture of the Taxus Genus Plant(I)

To 8 kg of biomass obtained from the tissue culture of Taxus genus plant was added 8 L of 95% (v/v) methanol, stirred at room temperature for 30 min, and filtered to give a methanol extract. Extraction was repeated 3 times, and the methanol extracts obtained from each time were pooled and concentrated at 35° C. under a reduced pressure of 30 mmHg, to give 4 L of methanol extract concentrate. Purity of taxol in the methanol extract was 0.24% and recovery was 100%. To the concentrated methanol extract was added 1.5 L of dichloromethane, stirred at room temperature for 15 min, and left to stand to obtain dichloromethane extract, and the extraction was repeated 3 times. Purity of taxol the crude extract was 2.4% and recovery was 100%.

The crude extract was dried at 35° C. under a pressure of 30 mmHg, and 15 g of the extract was dissolved in 56 ml of dichloromethane. Then, to the resultant solution was added 35 g of the synthetic adsorbent of active clay, stirred at 40° C. for 20 min and filtered to obtain filtrate. The filtrate thus obtained was washed with 285 ml of dichloromethane 3 times and washings were combined with the filtrate. Then, the filtrate thus combined was concentrated at 35° C. under a reduced pressure of 20 mmHg, to obtain 100 ml of final concentrate. Purity of the extract was 3.1% and recovery was 97%. 100 ml of dichloromethane extract was added to 1 L of hexane to obtain the precipitate, and filtered to give crude taxol of 23% purity (recovery 95%).

1 g of crude taxlol thus obtained was dissolved in 28.75 ml of methanol, and to the solution was added 17.25 ml of distilled water and left to stand at 4° C. for 2 days to obtain crystallized taxol. Then, the resultant solution was filtered with a 0.4μm filter and dried at 35° C. for 2 hrs under a vacuum condition, to give 299 mg of taxol powder of 70% purity (recovery 91%).

299 mg of taxol powder dissolved in 3 ml of methanol was injected to an ODS $C_{18}$ column (φ50×500 mm), and eluted with a mixture of methanol and water of 65:35 (v/v) under an assay condition summarized in Table 2 below. Then, the eluates were analyzed by UV detector by determining absorbances at 227 nm and active fractions having retention time (Rt) of 40 to 70 min were collected. Purity of taxol was 90% and recovery was 90%. Taxol containing fractions were dried at 35° C. under a reduced pressure of 10 mmHg. 209.3 mg of sample was dissolved in 2 ml of dichloromethane and injected to a silica column and eluted with a mixture of dichloromethane and methanol of 100:1.2 (v/v) under an assay condition summarized in Table 3 below. Then, the eluates were analyzed by UV detector and active fractions containing taxol were collected, dried by rotary evaporator, and vacuum dried to give 170.5 mg of crystallized taxol (purity 99.5%).

TABLE 2

| Assay condition for HPLC employing ODS column | |
| --- | --- |
| Instrument | Waters Delta Prep 4000 HPLC (Waters, U.S.A.) |
| Column | ODS $C_{18}$ column (φ50 mm ± 500 mm, Shiseido, Japan) |
| Fluid speed | 80 ml/min |
| Injection volume | 299 mg/3 ml (in methanol) |
| Detector | UV (227 nm) |

TABLE 3

| Assay condition for HPLC employing silica column | |
| --- | --- |
| Instrument | Waters Delta Prep 4000 HPLC (Waters, U.S.A.) |
| Column | Silica column (φ50 mm ± 500 mm, Shiseido, Japan) |
| Fluid speed | 80 ml/min |
| Injection volume | 209.3 mg/2 ml (in $CH_2Cl_2$) |
| Detector | UV (227 nm) |

EXAMPLE 2
Purification of Taxol from the Tissue Culture of the Taxus Genus Plant(II)

Taxol was purified from the tissue culture of the Taxus genus plant analogously as in Example 1, with the exception of solvent extraction employing dichloromethane/methanol, methanol and hexane: To 10 kg of biomass of Taxus genus plant was added 45 L of dichloromethane/methanol mixture (9:1, v/v), stirred at room temperature for 20 to 60 min, preferably 30 to 40 min and filtered to give a dichloromethane/methanol extract. Then, the extraction and concentration were carried out analogously as in the solvent extraction of Example 1. 100 g of the concentrated extract was dissolved in 100 ml of methanol, to obtain a methanol extract. Purity of taxol in the methanol extract was 0.59% and recovery was 95%. 100 ml of the methanol extract was added to 1 L of hexane, stirred at room temperature for 15 min and left to stand, and followed by the removal of hexane layer 3 times, to obtain a crude extract. Purity of taxol in the crude extract was 2.8% and recovery was 100%.

HPLC. analysis of taxol finally obtained revealed 99.5% purity and 90% recovery.

EXAMPLE 3
Purification of Taxol from the Leaf or Bark of Taxus Genus Plant(I)

Taxol crystal was purified analogously as in Example 1, with the exception of employing the chopped and powdered leaf or bark of Taxus genus plant as starting material. HPLC. analysis of taxol finally obtained revealed 99.6% purity and 96% recovery.

EXAMPLE 4
Purification of Taxol from the Leaf or Bark of Taxus Genus Plant(II)

Taxol crystal was purified analogously as in Example 2, with the exception of employing the chopped and powdered leaf or bark of Taxus genus plant as starting material. HPLC. analysis of taxol finally obtained revealed 99.6% purity and 90.5% recovery.

EXAMPLES 5 to 6

Taxol crystal was purified analogously as in Examples 1 and 3, with the exception of using 32 L of methanol and lengthening stirring time to 40 min in the methanol extraction step. HPLC. analysis revealed 99.6% purity.

EXAMPLES 7 to 8

Taxol crystal was purified analogously as in Examples 1 and 3, with the exception of using 4 L of dichloromethane and lengthening stirring time to 20 min in the methanol/dichloromethane extraction step. HPLC analysis revealed 99.5% and 96% purity, respectively.

EXAMPLES 9 to 10

Taxol crystal was purified analogously as in Examples 1 and 3, with the exception of employing methanol instead of dimethylsulfoxide as a solvent for dissolution of sample in the HPLC step HPLC. analysis revealed 99% and 97% purity, and 91%, 92% recovery, respectively.

Comparative Example

Taxol powder was obtained analogously as in Example 1, with the exception of skipping the active clay treatment and fractional precipitation steps. HPLC. analysis revealed about 40% purity.

As clearly illustrated and demonstrated above, the present invention provides a method for mass production of taxol from Taxus genus plant with a high purity of over 99% and a high recovery of over 90%, by employing a series of solvent extractions, adsorbent treatment, fractional precipitation and high performance liquid chromatography.

What is claimed is:

1. A method for mass production of high purity taxol from Taxus genus plant, which comprises the steps of:
   (i) extracting biomass from Taxus genus plant with an organic solvent selected from the group consisting of methanol, dichloromethane, and mixtures thereof to obtain a crude extract;
   (ii) treating said crude extract with active clay to remove tar from said extract;
   (iii) filtering the active clay-treated extract to give a filtrate;
   (iv) adding said filtrate to a sufficient amount of hexane to precipitate crude taxol;
   (v) dissolving said crude taxol in alcohol to produce an alcoholic taxol solution;
   (vi) adding water to said alcoholic taxol solution, thereby fractionally precipitating the crude taxol to obtain a precipitate and drying the precipitate to obtain taxol powder;
   (vii) dissolving the taxol powder in organic solvent;
   (viii) subjecting the taxol powder to reverse phase HPLC employing a hydrophobic resin column to obtain taxol-containing fractions;
   (ix) subjecting the taxol from said taxol-containing fractions to normal phase HPLC employing a silica column; and
   (x) recovering the taxol subjected to said normal phase HPLC.

2. The method of claim 1, wherein the biomass from Taxus genus plant is the chopped and powdered leaf or bark, or the cake of cell mass obtained in tissue culture of Taxus genus plant.

3. The method of claim 1, wherein the Taxus genus plant is selected from the group consisting of *Taxus brevifolia, Taxus canadensis, Taxus cuspidata, Taxus baccata, Taxus globosa, Taxus floridana, Taxus wallichiana, Taxus media* and *Taxus chinensis*.

4. The method of claim 1, wherein the solvent extraction of step (i) is carried out by: the addition of biomass of Taxus genus plant to methanol at a ratio of 20 to 200% (w/v), stirring at room temperature and filtering to obtain a methanol extract; and, the addition of dichloromethane to the methanol extract; and, the addition of dichloromethane to the methanol extract at a volume ratio of 10 to 50%, stirring and leaving to stand to obtain a crude extract.

5. The method of claim 1, wherein the solvent extraction of step (i) is carried out by: the addition of biomass of Taxus genus plant to a mixture of dichloromethane/methanol at a ratio of 10 to 100% (w/v), stirring at room temperature and filtering to obtain a dichloromethane/methanol extract; the dissolution of said extract in methanol at a ratio of 50 to 200% (w/v) to obtain a methanol extract; and, the addition of said extract to hexane at a volume ratio of 5 to 30%, stirring and leaving to stand to obtain a crude extract by the removal of hexane layer.

6. The method of claim 5, wherein dichloromethane and methanol are mixed at a volume ratio of 7:3 to 9:1.

7. The method of claim 1, wherein the active clay treatment of step (ii) is carried out by the addition of active clay to the crude extract at a ratio of 10 to 200% (w/w), stirring and filtering according to step (iii) to obtain filtrate.

8. The method of claim 1, wherein the crude taxol precipitation of step (iv) is carried out by the addition of the filtrate in dicholoromethane to 500 to 1,500% volume of hexane.

9. The method of claim 1, wherein the fractional precipitation of step (vi) is carried out by the dissolution of the crude taxol in a mixture of methanol and water at a ratio of 1 to 10% (w/v) and leaving to stand at −20 to 10° C. for 1 to 3 days.

10. The method of claim 9, wherein methanol and water are mixed at a volume ratio of 2:1 to 1:1.

11. The method of claim 1, wherein the HPLC employing a hydrophobic resin column of step (viii) is carried out by the injection of taxol powder dissolved in organic solvent at a ratio of 0.5 to 10% (w/v) to ODS (octadecylsilylated, $C_{18}$) column.

12. The method of claim 11, wherein the organic solvent is dimethylsulfoxide or methanol.

13. The method of claim 11, wherein said ODS column is eluted with a mixture of methanol and water mixed at a volume ratio of 1:0.3 to 1:0.8.

14. The method of claim 1, wherein said silica column employed in step (ix) is eluted with a mixture of dichloromethane and methanol mixed at a volume ratio of 95:5 to 99:1.

15. The method of claim 1, which further comprises, after step (i) and before step (ii),
 (a) drying said crude extract; and
 (b) adding an effective amount of dichloromethane to dissolve said crude extract.

* * * * *